US00PP32745P3

(12) United States Plant Patent
Mazzardis

(10) Patent No.: US PP32,745 P3
(45) Date of Patent: Jan. 12, 2021

(54) BLUEBERRY PLANT NAMED 'NS 13-5'

(50) Latin Name: ***Vaccinium* hybrid**
Varietal Denomination: NS 13-5

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd, Subiaco (AU)

( * ) Notice: Subject to any disclaimer, the term of this patent is extended or adjusted under 35 U.S.C. 154(b) by 0 days.

(21) Appl. No.: 16/602,549

(22) Filed: Oct. 29, 2019

(65) Prior Publication Data

US 2020/0170157 P1 May 28, 2020

(30) Foreign Application Priority Data

Nov. 22, 2018 (QZ) ..... PBR 2018/3061

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Randall Danskin, P.S.

(57) ABSTRACT

A new and distinct variety of blueberry plant, which is denominated varietally as 'NS 13-5' is described, with a strong vigor and straight sepals and which produces large to very large fruit, which is high in acidity, under the ecological conditions prevailing in Yanchep, Western Australia.

6 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 13-5'.

CROSS REFERENCE TO RELATED APPLICATIONS

This application claims the benefit of priority under 35 USC § 119 to Community Plant Variety Office (CPVO) Application No. 2018/3061 for Community Plant Variety Rights, filed on Nov. 22, 2018 for a blueberry plant with a variety denomination of 'NS 13-5', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 13-5' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant '7-26' (unpatented), and a pollen parent, blueberry plant '8-10' (unpatented) during the 2012 growing season.

Prior Varieties. The seed parent '7-26' is characterized principally by a semi-upright growth habit, a medium vigor, an early season first pick date, and further produces large-sized, medium firmness, high sweetness, and low acidity fruit under the ecological conditions occurring in Yanchep, Western Australia. The seed parent '7-26' is semi-evergreen and produces fruit on one-year old shoots only. The pollen parent '8-10', on the other hand, is characterized principally by a semi-upright growth habit, a strong vigor, an early season first pick date, and further produces large-sized, firm, high sweetness, and medium acidity fruit under the ecological conditions occurring in Yanchep, Western Australia. The pollen parent '8-10' is semi-evergreen and produces fruit on one-year old shoots only.

Origin. The seed from the seed parent '7-26' produced approximately 700 plants following cross-pollination. These new plants were then grown at the aforementioned property, and fruit from these new plants was first observed in 2013. A subsequent assessment of these same self-fertile, new plants conducted during the 2014 growing season led to selecting the 'NS 13-5' variety for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2015 growing season led to a conclusion that the 'NS 13-5' variety was a distinct and new variety of blueberry plant found to be true to the original plant. The new variety of blueberry plant was considered to be novel in view of its strong vigor, straight sepals, and large to very large fruit, which exhibited high acidity.

Comparisons. In comparison to the seed parent '7-26' under the ecological conditions occurring in Yanchep, Western Australia, the new variety has a noteworthy vigor. In this regard, the seed parent is considered to have a medium vigor.

However, the new variety of blueberry plant has a strong vigor. In addition, the seed parent produces fruit having a fruit size considered to be large. In contrast, the new variety of blueberry plant produces fruit considered to be large to very large. Further, the seed parent produces fruit considered to exhibit low acidity. This is in contrast to the fruit of the new variety of blueberry plant, which is considered to exhibit high acidity. Still further, the seed parent produces flowers with sepals considered to be incurving. This is in contrast to the flowers of the new variety of blueberry plant with sepals considered to be straight.

In comparison to the pollen parent '8-10' under the ecological conditions occurring in Yanchep, Western Australia, both the new variety and the pollen parent are considered to have a strong vigor. In addition, the pollen parent produces fruit having a fruit size considered to be large. In contrast, the new variety of blueberry plant produces fruit considered to be large to very large. Further, the pollen parent produces fruit considered to exhibit medium acidity. This is in contrast to the fruit of the new variety of blueberry plant, which is considered to exhibit high acidity. Still further, the pollen parent produces flowers with sepals considered to be incurving. This is in contrast to the flowers of the new variety of blueberry plant with sepals considered to be straight.

The new variety of blueberry plant is readily distinguishable from the most closely related, known variety, the 'EB 9-4' blueberry plant described in U.S. Plant Pat. No. 28,334, which is herein incorporated by reference in its entirety. In this regard, the closest known variety 'EB 9-4' has a vigor considered to be medium under the ecological conditions prevailing in Yanchep, Western Australia. In contrast, the new variety of blueberry plant has a vigor considered to be strong. In addition, both the closest known variety and the new variety of blueberry plant produce fruit having a fruit size considered to be large to very large for the species. Further, the closest known variety produces fruit having a fruit acidity considered to be low to medium. This is in contrast to the new variety, which produces high acidity fruit. Still further, the closest known variety produces flowers with sepals considered to be incurving. This is in contrast to the flowers of the new variety of blueberry plant with sepals considered to be straight.

The comparisons described above are summarized in the table below.

| | 'NS 13-5' | 'EB 9-4' | '7-26' (Seed) | '8-10' (Pollen) |
|---|---|---|---|---|
| Plant vigor | Strong | Medium | Medium | Strong |
| Fruit size | Large to very large | Large to very large | Large | Large |
| Fruit acidity | High | Low to medium | Low | Medium |
| Type of sepal | Straight | Incurving | Incurving | Incurving |

BRIEF DESCRIPTION OF THE DRAWINGS

The accompanying drawings are color photographs of the new blueberry plant 'NS 13-5' during the third year of growth under the ecological conditions prevailing at the breeder's property, which is located at Yanchep Springs in Yanchep, Western Australia.

Figure 1:
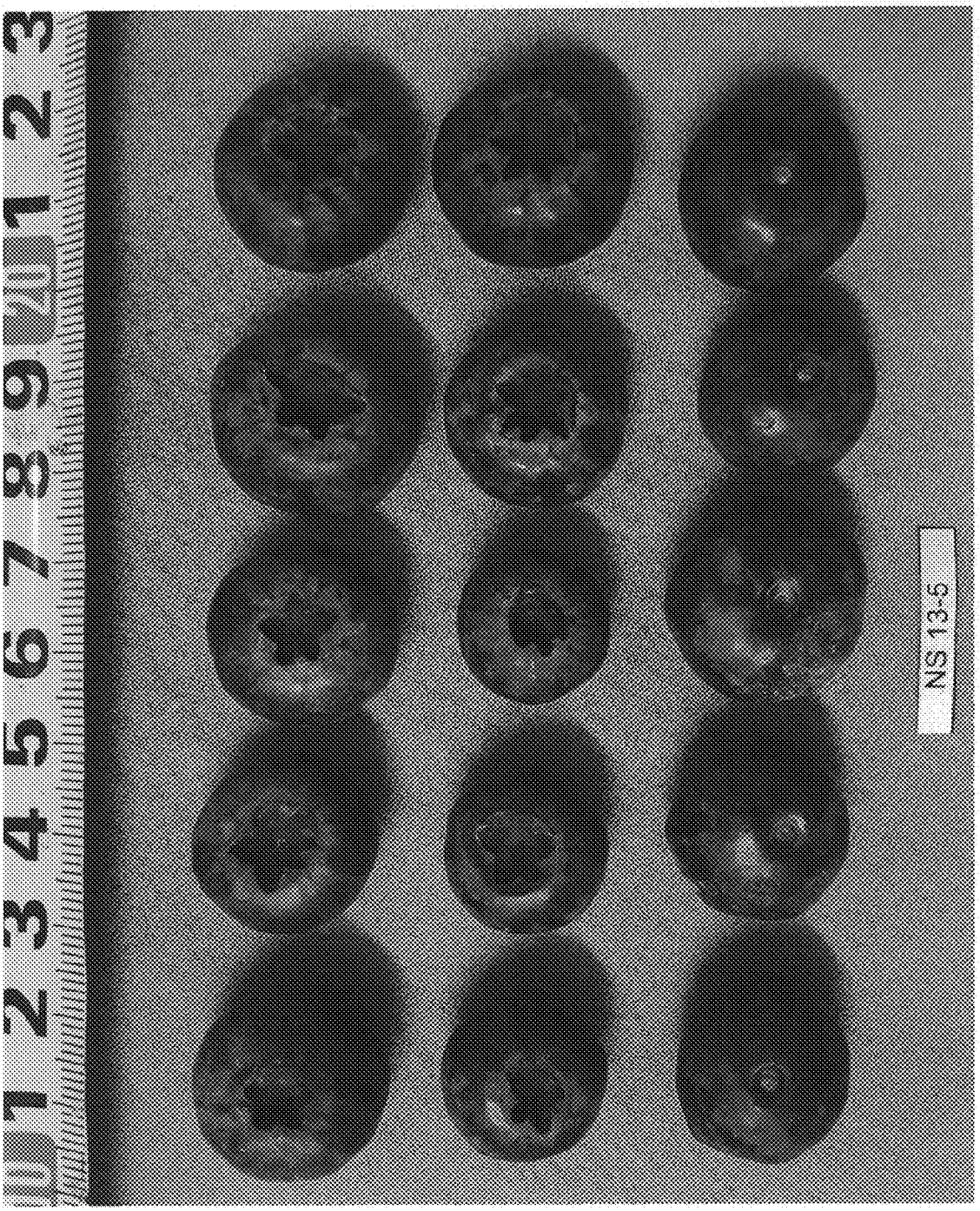
FIG. 1 is a color photograph, which shows fruit of the new blueberry plant 'NS 13-5', the fruit being sufficiently mature for harvesting and shipment. This photograph also depicts the large to very large fruit size and the color of the ripe fruit.
Figure 2:
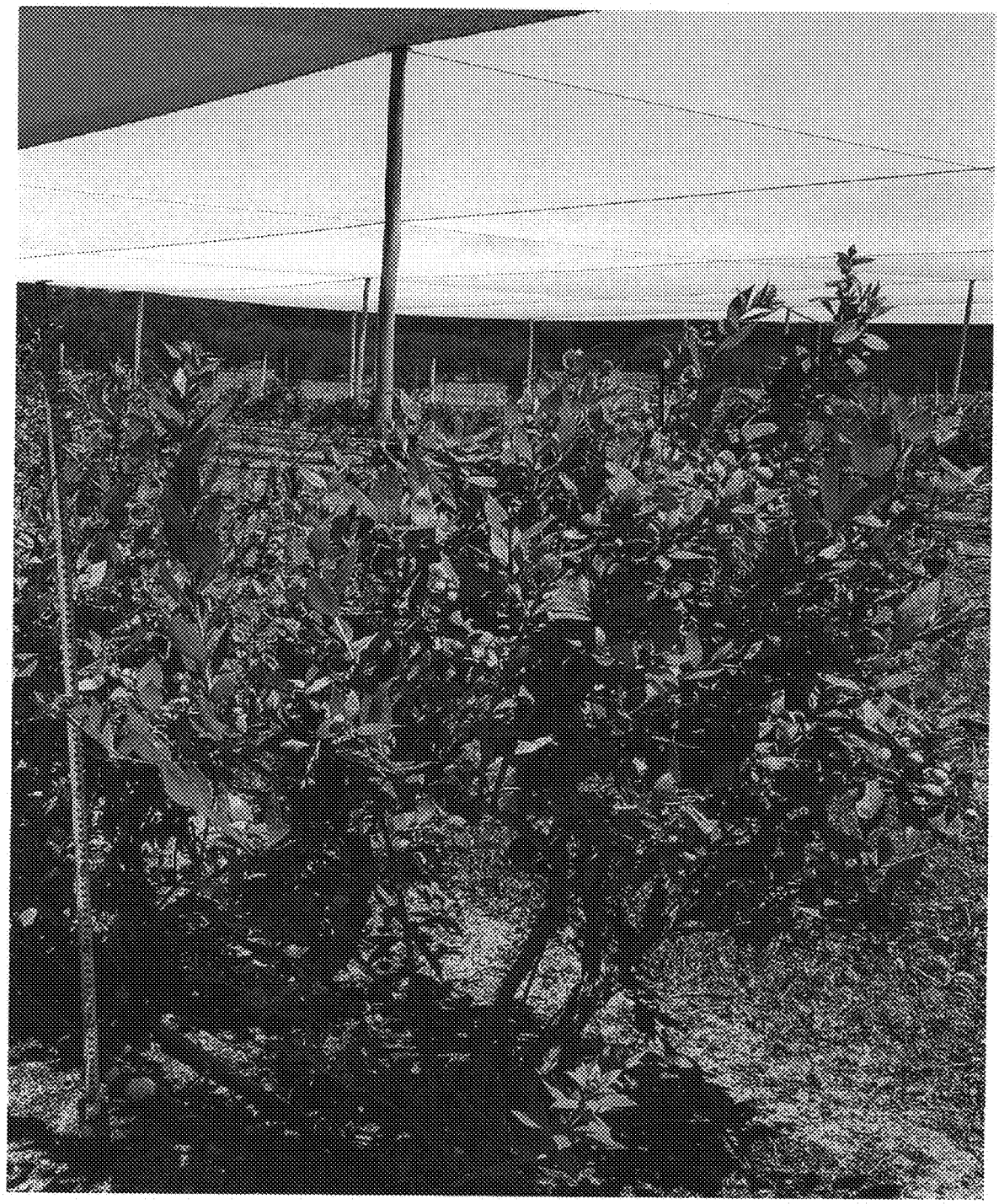
FIG. 2 is a color photograph, which shows the new blueberry plant 'NS 13-5'. This photograph depicts a mature bush with ripe and unripe fruits, the large to very large fruit size, and the upright to semi-upright growth habit of the bush. The ripe fruit is sufficiently mature for harvesting and shipment.
Figure 3:
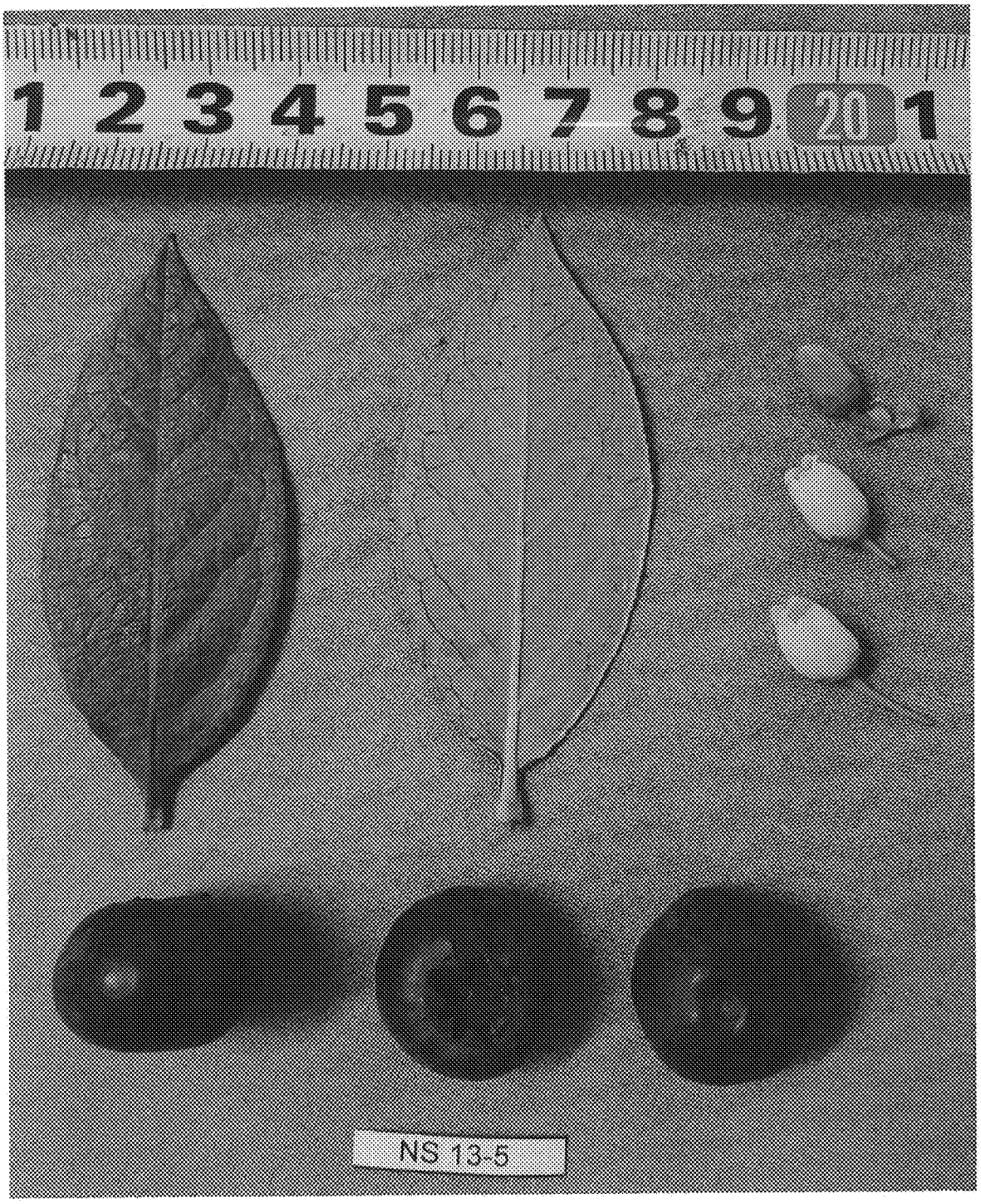
FIG. 3 is a color photograph, which shows the leaves, blooms, and fruit of the new blueberry plant 'NS 13-5'. This photograph depicts the side, under side, and upper, respectively, of three ripe fruits, the fruits being sufficiently mature for harvesting and shipment. This photograph further shows the upper and under side coloration of two leaves, and three blooms at different stages of maturation, along with the sizes of the leaves, blooms, and fruit.
Figure 4:
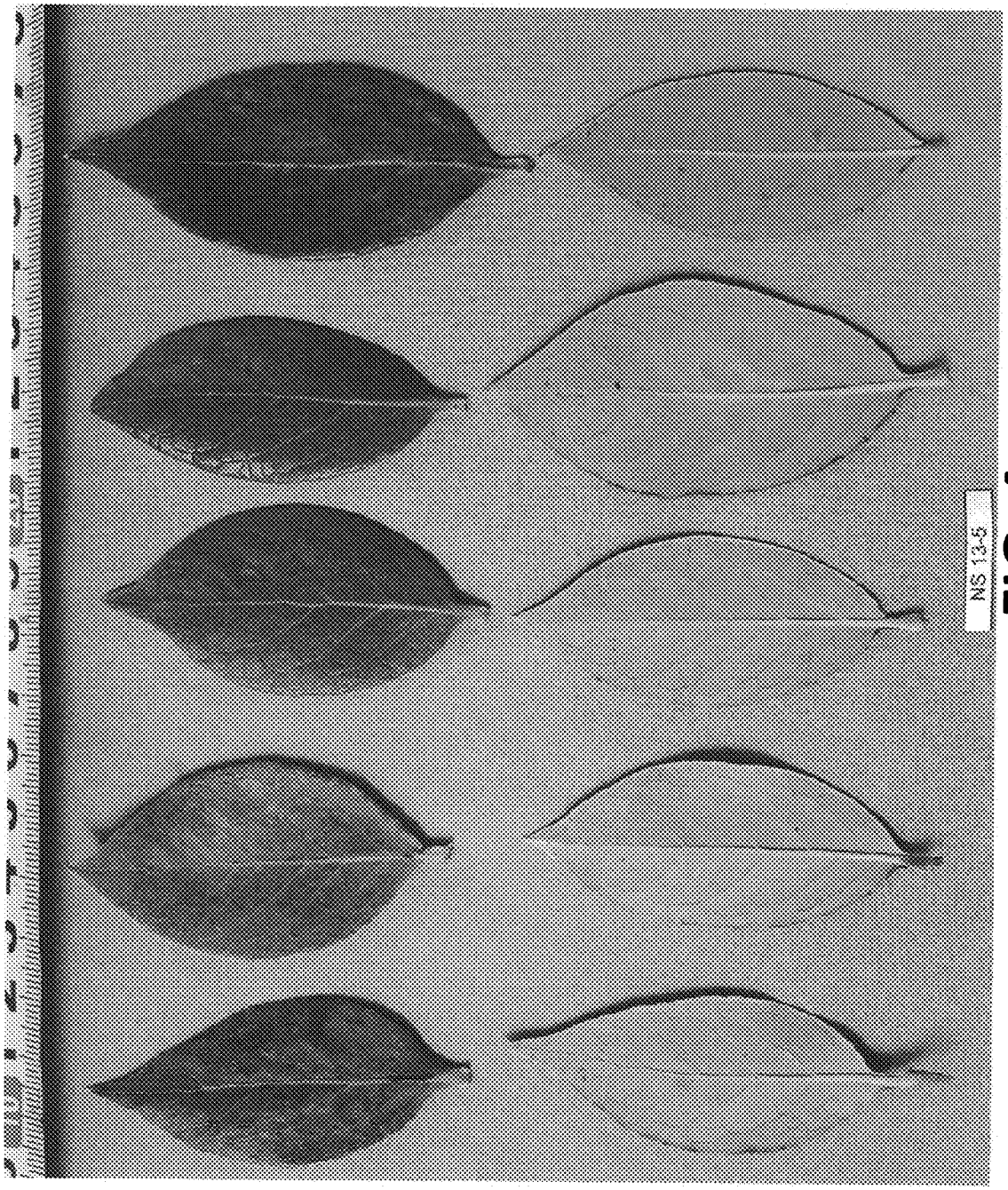
FIG. 4 is a color photograph, which shows the leaves of the new blueberry plant 'NS 13-5'. This photograph depicts several leaves showing the sizes and the upper and under side colorations thereof.
Figure 5:
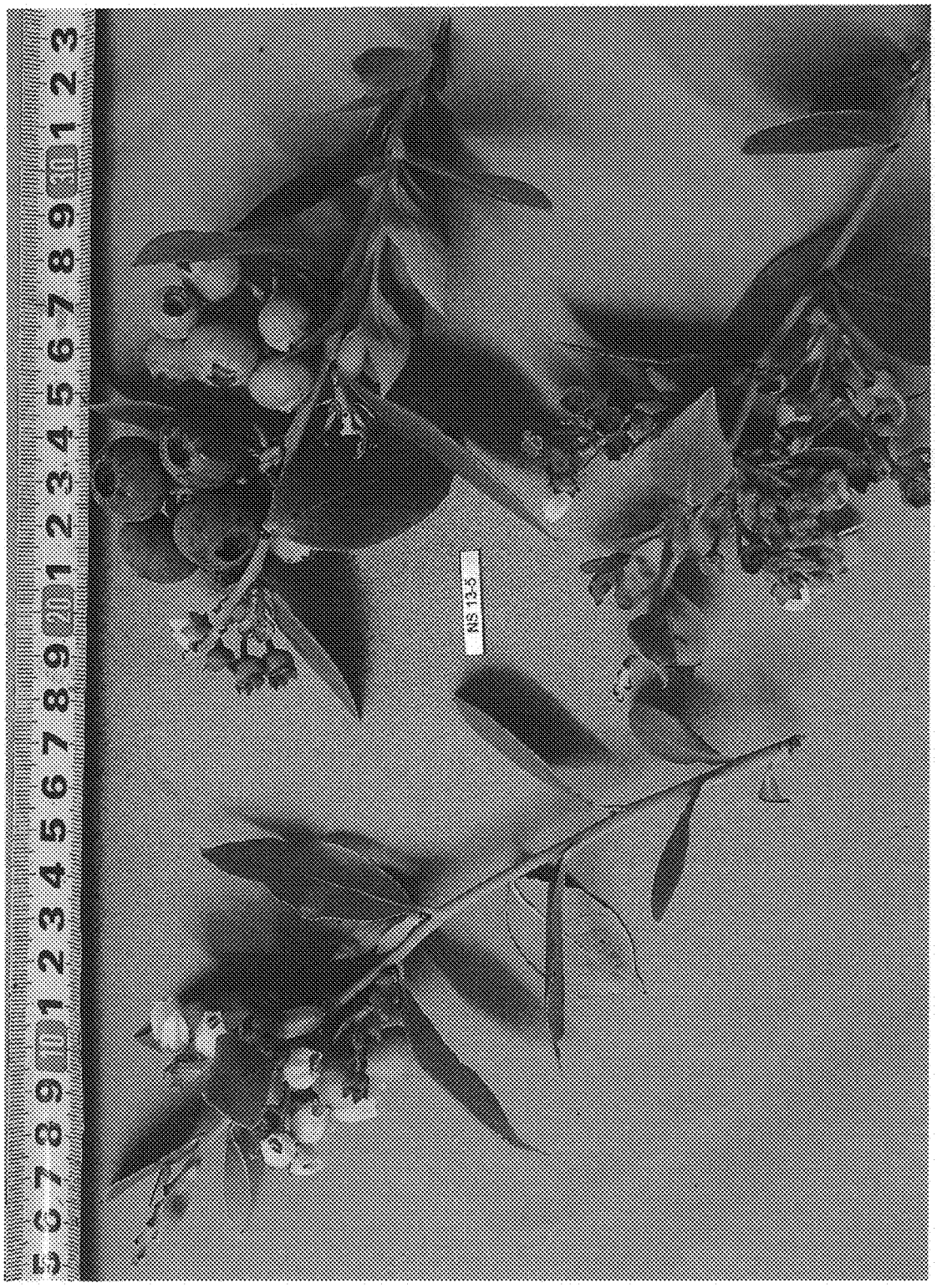
FIG. 5 is a color photograph, which shows portions of three vegetative stems bearing leaves, blooms, and fruit of the new blueberry plant 'NS 13-5'. This photograph depicts four ripe fruits, the fruits being sufficiently mature for harvesting and shipment, and further shows leaves at different stages of maturation, the upper and under side coloration thereof, and fruit and blooms at different stages of maturation.
Figure 6:
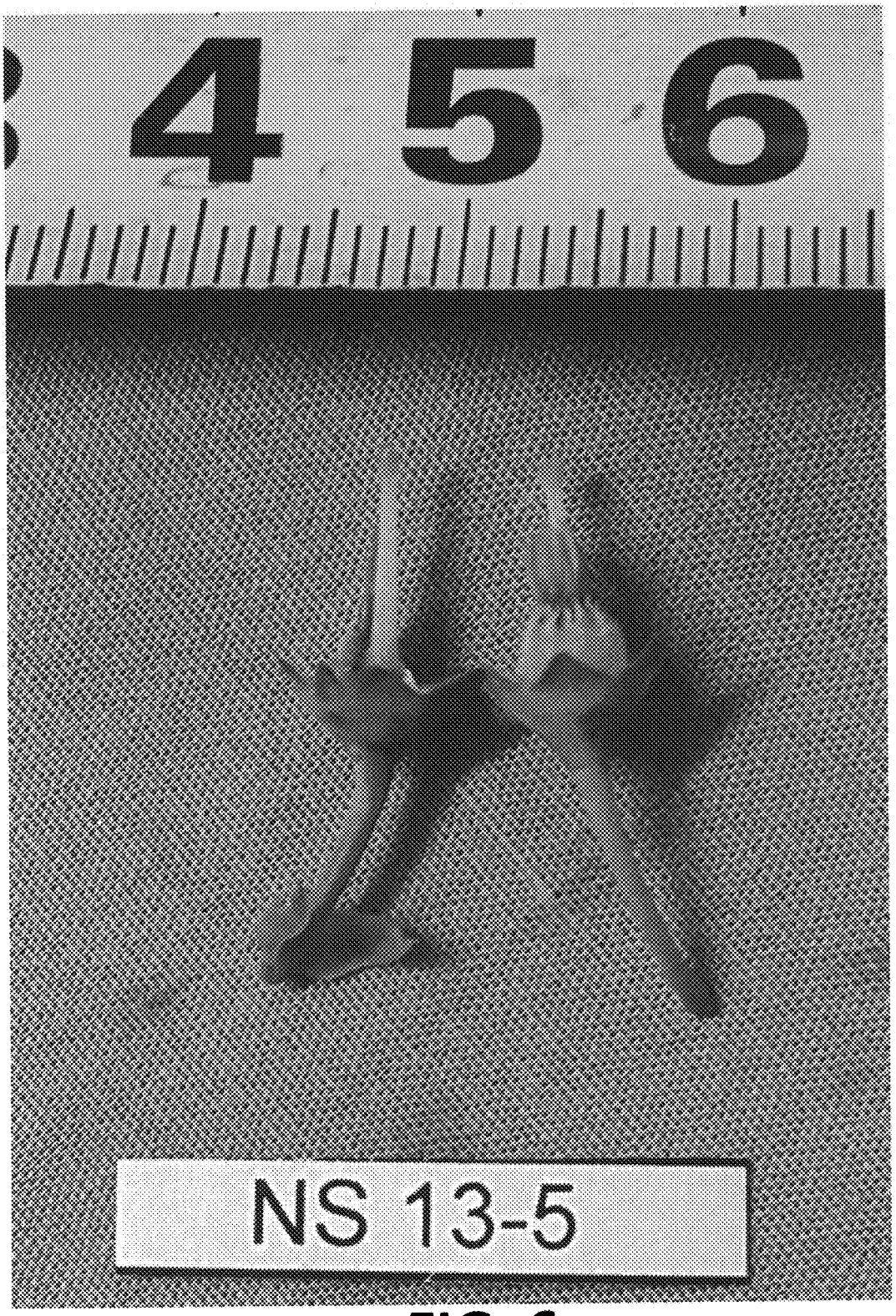
FIG. 6 is a color photograph, which shows two immature fruits of the new blueberry plant 'NS 13-5'. This photograph depicts one fruit shortly after corolla fall and one fruit shortly before corolla fall, showing the sizes thereof.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition, hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor.*—Considered strong for the species. This is in contrast to the seed parent '7-26', wherein the plant vigor is only considered medium. This is also in contrast to the closest known variety 'EB 9-4', wherein the plant vigor is only considered medium.

*Growth habit.*—Considered upright to semi-upright. This is in comparison to the commercial variety 'Ivanhoe' (unpatented), which is considered to be upright, and the commercial variety 'Bluetta' (unpatented), which is considered to be semi-upright.

*Average size of plant.*—1.2 meters in height by 1 meter in width.

*Internode length (space between nodes).*—Considered medium to long, 25 to 30 millimeters (mm).

*Bark color.*—RHS Grey Reddish Brown Group 177C.

*Color, one year old shoots.*—RHS Light Yellow Green Group 145B.

*Fruiting type.*—On one-year-old shoots and current season's shoots, in like manner to commercial varieties 'Concord' (unpatented) and 'Burlington'(unpatented).

Foliage: General.

*Average leaf length.*—Considered medium to long for the species, 62.5 mm.

*Average leaf width.*—Considered medium to broad for the species, 29.8 mm.

*Color of leaf upper.*—RHS Green Group NN137A.

*Color of leaf underside.*—RHS Green Group 138C.

*Vein color of plant leaf.*—RHS Light Yellow Green Group 145B.

*Venation pattern of leaf.*—Pinnate reticulate.

*Leaf apex texture.*—Glabrous.

*Leaf apex shape.*—Apex.

*Leaf base shape.*—Apex.

*Leaf shape.*—Elliptic.

*Leaf margin.*—Entire.

*Leaf arrangement of plant.*—Alternate.

Flowers:

*Number of flowers per inflorescence.*—5.

*Average length of inflorescence (excluding peduncle).*—Considered medium, 15 mm.

*Corolla shape.*—Urceolate.

*Corolla tube surface texture.*—Ridges are present on the corolla tube.

*Average corolla size.*—Considered medium, 10 mm in length by 7 mm in width.

*Corolla diameter.*—7 to 10 mm.

*Average corolla aperture size.*—4.80 mm.

*Corolla color.*—RHS White Group NN155D.

*Pedicel color.*—RHS Green Group 142C.

*Average pedicel length.*—8.70 mm.

*Average calyx diameter.*—Considered large to very large, 9.4 mm.

*Average calyx basin depth.*—Considered deep, 2.59 mm.

*Attitude of sepals.*—Considered erect.

*Type of sepals.*—Considered straight. This is in contrast to the seed parent '7-26' and pollen parent '8-10', wherein the type of sepals is considered incurving. This is in further contrast to the closest known variety 'EB 9-4', wherein the type of sepals is considered incurving.

Reproductive organs:

*Average size of pollen anthers.*—8.37 mm.

*Color of pollen anthers.*—RHS Moderate Reddish Orange Group N172A.

*Average pistil length.*—10.19 mm.

*Pistil color.*—RHS Light Yellow Green Group 145B.

Fruit:

*Color of unripe fruit.*—RHS Strong Yellow Green Group 145A.

*Color of fruit skin.*—RHS Bluish Black Group 203C, also considered "dark blue" in like color to the commercial variety 'Heerma' (unpatented), after removal of bloom.

*Color of ripe fruit flesh.*—RHS Light Yellow Green Group 145C.

*Color of seeds.*—RHS Strong Orange Group 168B.

*Average fruit size.*—Considered large to very large, 20.1 mm in diameter and 14.73 mm in height. This is in contrast to the seed parent '7-26' and pollen parent '8-10', wherein the fruit size is only considered large. Fruit size of the closest known variety 'EB 9-4' is also considered large to very large.

*Average weight of fruit.*—3 grams.

*Average fruit production.*—5-7 kilograms on a three-year-old bush.

*Berry shape.*—Considered oblate.

*Sweetness when ripe.*—Considered high for the species.

*Firmness when ripe.*—Considered firm for the species.

*Acidity when ripe.*—Considered high for the species. This is in contrast to the seed parent '7-26', wherein the fruit acidity is only considered low, and the pollen parent '8-10', wherein the fruit acidity is only considered medium. This is in further contrast to the closest known variety 'EB 9-4', wherein the fruit acidity is considered low to medium.

*Cluster density.*—Considered medium for the species.

*Storability of fruit.*—Considered excellent for the species.

*Market use of fruit.*—1st grade fresh market fruit.

*Date of bud burst.*—This variety is evergreen, effectively with buds, flowers, and fruit throughout the whole of the year under the ecological conditions prevailing in Yanchep, Western Australia.

*Date of vegetative bud burst.*—Early August under the ecological conditions prevailing in Yanchep, Western Australia.

*Date of bloom time.*—February for one-year-old shoot otherwise dormant during the Summer under the ecological conditions prevailing in Yanchep, Western Australia. Also, considered very early on one-year old shoot in like manner to the commercial variety 'Patriot' (unpatented) and considered very early on current year's shoot before the commercial variety 'O'Neal' (unpatented), which is considered early.

*Duration of bloom time and bloom intensity.*—12 weeks for one-year-old shoot otherwise dormant during the Summer under the ecological conditions prevailing in Yanchep, Western Australia; bloom intensity is considered strong.

*Beginning of fruit ripening.*—Considered very early on one-year-old shoot in like manner to the commercial variety 'Bluetta' (unpatented) and considered very early on current year's shoot prior to the commercial variety 'O'Neal' (unpatented), which is considered early.

*First pick date.*—April for one-year-old shoot otherwise dormant during the Summer under the ecological conditions prevailing in Yanchep, Western Australia.

*Last pick date*.—December under the ecological conditions prevailing in Yanchep, Western Australia.

*Pollination requirements*.—Self-fertile.

*Resistance to pests and disease*.—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant, substantially as illustrated and described, which is characterized principally as to novelty by a strong vigor, by straight sepals, and by producing fruit considered large to very large in size and high in acidity under the ecological conditions prevailing in Yanchep, Western Australia.

* * * * *